(12) United States Patent
Rivlin et al.

(10) Patent No.: US 10,905,783 B2
(45) Date of Patent: Feb. 2, 2021

(54) GLUCOSAMINE AND DERIVATIVES THEREOF IN IMAGING

(71) Applicants: Michal Rivlin, Hod Hasharon (IL); Gil Navon, Tel Aviv (IL)

(72) Inventors: Michal Rivlin, Hod Hasharon (IL); Gil Navon, Tel Aviv (IL)

(73) Assignees: Michal Rivlin, Hod Hasharon (IL); Gil Navon, Tel Aviv (IL)

( * ) Notice: Subject to any disclaimer, the term of this patent is extended or adjusted under 35 U.S.C. 154(b) by 373 days.

(21) Appl. No.: 15/778,946

(22) PCT Filed: Nov. 27, 2016

(86) PCT No.: PCT/IL2016/051270
§ 371 (c)(1),
(2) Date: May 24, 2018

(87) PCT Pub. No.: WO2017/090047
PCT Pub. Date: Jun. 1, 2017

(65) Prior Publication Data
US 2018/0344879 A1  Dec. 6, 2018

Related U.S. Application Data

(60) Provisional application No. 62/260,370, filed on Nov. 27, 2015.

(51) Int. Cl.
*A61B 5/00* (2006.01)
*A61K 49/10* (2006.01)
(Continued)

(52) U.S. Cl.
CPC ............ *A61K 49/10* (2013.01); *A61B 5/0033* (2013.01); *A61B 5/0036* (2018.08);
(Continued)

(58) Field of Classification Search
CPC .... A61K 49/10; A61B 5/0036; A61B 5/0033; A61B 5/4848; A61B 6/037; A61B 6/481;
(Continued)

(56) References Cited

U.S. PATENT DOCUMENTS 7,008,633 B2   3/2006   Yang et al.
7,449,316 B2   11/2008  Clausen et al.
(Continued)

FOREIGN PATENT DOCUMENTS

EP   0 143 840 B1   6/1985
EP   0 466 838 B1   4/1998
(Continued)

OTHER PUBLICATIONS

Rivlin et al., "Molecular imaging of tumors and metastases using chemical exchange saturation transfer (CEST) MRI", Scientific Reports, vol. 3, No. 3045, pp. 1-7, (2013).
(Continued)

*Primary Examiner* — Joel Lamprecht
(74) *Attorney, Agent, or Firm* — Vorys, Sater, Seymour and Pease LLP; Anthony Venturing (57) ABSTRACT

Provided are formulations including a contrast agent selected from glucosamine, a salt thereof and a glucosamine derivative, for use in imaging.

9 Claims, 8 Drawing Sheets

(51) Int. Cl.
*A61B 5/055* (2006.01)
*A61B 6/03* (2006.01)
*A61B 6/00* (2006.01)
*A61B 8/08* (2006.01)
*A61B 6/12* (2006.01)

(52) U.S. Cl.
CPC ............ *A61B 5/0071* (2013.01); *A61B 5/055* (2013.01); *A61B 5/4848* (2013.01); *A61B 6/037* (2013.01); *A61B 6/481* (2013.01); *A61B 8/481* (2013.01); *A61B 6/12* (2013.01); *A61B 8/085* (2013.01)

(58) Field of Classification Search
CPC ....... A61B 8/481; A61B 5/0071; A61B 5/055; A61B 8/085; A61B 6/12
See application file for complete search history.

(56) References Cited

U.S. PATENT DOCUMENTS

| | | | |
|---|---|---|---|
| 8,003,392 | B2 | 8/2011 | Chen et al. |
| 8,147,805 | B2 | 4/2012 | Yang et al. |
| 8,226,619 | B2 | 7/2012 | Miller et al. |
| 9,180,211 | B2 | 11/2015 | Van Zijl et al. |
| 2005/0106597 | A1 | 5/2005 | Choi |
| 2005/0255038 | A1 | 11/2005 | Houck et al. |
| 2006/0142225 | A1 | 6/2006 | McSwiggen |
| 2008/0107598 | A1 | 5/2008 | Yang et al. |
| 2008/0159959 | A1 | 7/2008 | Wang et al. |
| 2009/0087377 | A1 | 4/2009 | Azhdarinia et al. |
| 2010/0028326 | A1 | 2/2010 | Kopchick et al. |
| 2011/0171136 | A1 | 7/2011 | Poss et al. |
| 2012/0019245 | A1 | 1/2012 | Reddy et al. |
| 2012/0276005 | A1 | 11/2012 | Yang et al. |
| 2014/0274768 | A1 | 9/2014 | Haab |
| 2015/0086484 | A1* | 3/2015 | Hanes .................. A61K 31/704 424/9.3 |
| 2016/0206760 | A1* | 7/2016 | Yu ...................... A61K 49/1878 |

FOREIGN PATENT DOCUMENTS

| | | |
|---|---|---|
| EP | 0 932 696 B1 | 12/2004 |
| EP | 1 986 010 A1 | 10/2008 |
| EP | 2 205 972 B1 | 1/2012 |
| EP | 1 286 704 B1 | 7/2014 |
| WO | 03/082301 A1 | 10/2003 |
| WO | 2006/074546 A1 | 7/2006 |
| WO | 2008/036842 A2 | 3/2008 |
| WO | 2008/143944 A2 | 11/2008 |
| WO | 2009/016180 A2 | 2/2009 |
| WO | 2009/037337 A1 | 3/2009 |
| WO | 2012/082874 A2 | 6/2012 |
| WO | 2014/122664 A1 | 8/2014 |
| WO | 2014/124006 A1 | 8/2014 |
| WO | 2015/145447 A2 | 10/2015 |

OTHER PUBLICATIONS

Rivlin et al., "Functional Molecular Imaging of Tumors by Chemical Exchange Saturation Transfer MRI of 3-O-Methyl-D-Glucose", Magnetic Resonance in Medicine, vol. 72, pp. 1375-1380, (2014).
Berti et al., "Early Detection of Alzheimer's Disease with PET Imaging", Neurodegenerative Dis, vol. 7, pp. 131-135, (2010).
Anderson et al., "Glucosamine effects in humans: a review of effects on glucose metabolism, side effects, safety considerations and efficacy", Food and Chemical Toxicology, vol. 43, pp. 187-201, (2005).
Salazar et al., "Glucosamine for Osteoarthritis: Biological Effects, Clinical Efficacy, and Safety on Glucose Metabolism", Arthritis, vol. 2014, article id 432463, 13 pages, (2014).
Uldry et al., "GLUT2 is a high affinity glucosamine transporter", FEBS Letters, vol. 524, pp. 199-203, (2002).
Godoy et al., "Differential Subcellular Distribution of Glucose Transporters GLUT1-6 and GLUT9 in Human Cancer: Ultrastructural Localization of GLUT1 and GLUT5 in Breast Tumor Tissues", Journal of Cellular Physiology, vol. 207, pp. 614-627, (2006).
Setnikar et al., "Absorption, Distribution, Metabolism and Excretion of Glucosamine Sulfate", Arzneimittelforschung, vol. 51, No. 9, pp. 699-725, (2001).
Longo et al., "EXCI-CEST: exploiting pharmaceutical excipients as safe MRI-CEST contrast agents", Proc. Intl. Soc. Mag. Reson. Med., vol. 22, p. 2819, (2014).
Li et al., "A novel functional CT contrast agent for molecular imaging of cancer", Phys. Med. Biol., vol. 55, pp. 4389-4397, (2010).
Chan et al., "Natural D-Glucose as a biodegradable MRI contrast agent for detecting cancer", Magn Reson Med., vol. 68, No. 6, pp. 1764-1773, (2012).
Rivlin et al., "Glucosamine and N-acetyl glucosamine as new CEST MRI agents for molecular imaging of tumors", Scientific Reports, vol. 6, No. 32648, 7 pages, (2016).
Liu et al., "Nuts and Bolts of CEST MR imaging", NMR Biomed., vol. 26, No. 7, pp. 810-828, (2013).

* cited by examiner

FIG. 6A  Before treatment:

The tumor $T_2$ Rare (Conventional image)

FIG. 6B

CEST control @ t=0min 10%

FIG. 6C  Treatment: 0.38g/kg GluA, PO:

CEST @ t=11min 14.4%

FIG. 6D

Metastasis

CEST @ t=46min 14.7%

FIG. 7A Before treatment:
The tumor
The urinary bladder — $T_2$ Rare (Conventional image)

FIG. 7B
CEST control @ t=0min 11.6%

FIG. 7D
CEST @ t=60min 14.3%

Treatment: 0.38g/kg GluA, PO:

FIG. 7C
Metastasis
CEST @ t=15min 13.8%

FIG. 9A  FIG. 9B  FIG. 9C  FIG. 9D

GLUCOSAMINE AND DERIVATIVES THEREOF IN IMAGING

TECHNOLOGICAL FIELD

The invention generally concerns use of glucosamine and derivatives thereof in imaging.

BACKGROUND

Glucose and analogues thereof, such as 2-deoxy-D-glucose (2-DG) and 2-fluoro-deoxy-D-glucose (FDG) are known to be taken up preferentially by cancer cells, a phenomenon that is known as the "Warburg effect".

The positron emission tomography (PET) method makes use of the "Warburg effect" by imaging flouro-deoxy-D-glucose (FDG) containing the radioactive fluorine atom $^{18}$F. The CEST-MRI method enables to image glucose and glucose derivatives with enhanced sensitivity and these compounds were suggested to be used for cancer diagnosis. However, glucose gives inferior CEST signal due to its rapid conversion to lactic acid by glycolysis.

US 2012/0019245 [1] discloses using CEST MRI to monitor the concentration of various neurotransmitters and energy metabolites to characterize and monitor various disease states in the body, more specifically in the liver, brain and myocardium, correlated to the concentration of that metabolized.

Detection of administered sugar can employ CEST MRI due to the presence of the exchangeable protons in said sugar. WO 2012/082874 [2] discloses MRI methods for the detection of tissue physiological parameters in a subject by using non-labeled glucose to recognize whether at least one tissue-related parameter is abnormal.

Recently, the CEST MRI method has been shown to enable imaging of glucose with enhanced sensitivity and these compounds were suggested to be used for cancer diagnosis [3,4]. However, glucose gives inferior CEST signal due to its rapid conversion to lactic acid by glycolysis, and the two analogues 2-DG and FDG that undergo phosphorylation but do not undergo further metabolism are toxic at high concentrations such as 3 g/kg for 2-DG in rats.

The use of 3-O-methyl glucose (3OMG) for imaging tissue abnormalities was also described [5] by the inventors of the present application.

N-Acetyl-D-glucosamine has been shown to increase CEST contrast in both TSA and B16 cancer models [12].

BACKGROUND ART

[1] US 2012/0019245
[2] WO 2012/082874
[3] Rivlin M., et al., (2013), *Scientific Report* 3, Article number: 3045
[4] Rivlin M., et al., (2014), *Magn. Reson. Med* 72:1375-1380
[5] WO 2015/145447
[6] Berti et al., (2010), *Neurodegenerative Dis.* 7:131-135
[7] Anderson J., et al., (2005), *Food Chem Toxicol* 43: 187-201.
[8] Salazar J., et al., (2014), *Arthritis* 13.
[9] Uldry M., et al., (2002), *FEBS Letters* 524: 199-203.
[10] Godoy A., et al. (2006), *J. Cell. Physiol.* 207:614-627.
[11] Setnikar I., et al., (2001), *Arzneimittelforschung* 51: 699-725.
[12] European Molecular Imaging Meeting, Abstract: EXCI-CEST: exploiting pharmaceutical excipients as safe MRI-CEST contrast agents; Dario Livio Longo, et al., June 2014.

SUMMARY OF THE INVENTION

The inventors of the invention disclosed herein have realized the use of 2-amino-2-deoxy-glucose, glucosamine, its salts and derivatives thereof as contrast agents in imaging.

Glucosamine has been widely prescribed as a food supplement for therapeutic usage due to its lack of toxicity and unlike other glucosamine derivatives does not affect blood glucose levels or insulin sensitivity and therefore may be utilized in imaging of a large population, including diabetic patients or those sensitive to glucose levels.

Thus, the invention provides use of glucosamine and/or a derivative thereof, referred herein as "contrast agents", in methods of imaging, e.g., of at least one tissue abnormality. The imaging may be utilized for the purpose of detecting, diagnosing or monitoring a disease state, as further explained herein, in a subject or in a tissue/organ.

As used herein, any reference to "glucosamine" is meant also to include glucosamine salts and glucosamine derivatives, unless otherwise specifically excluded.

In a first aspect, the invention provides a formulation comprising a contrast agent selected from glucosamine, glucosamine salts and derivatives thereof. The glucosamine derivative is not an acetylglucosamine, e.g., N-acetyl-D-glucosamine.

In a further aspect, the invention provides a formulation, as herein, for use in imaging.

Glucosamine or any derivative thereof may be used, in accordance with the present invention, as contrast agent(s) in diagnostic formulations and may be administered to a subject whose imaging is required along with at least one diagnostically acceptable carrier and in a diagnostically effective amount. Thus, the invention further contemplates use of glucosamine and/or salt and/or a derivative thereof in the preparation of diagnostic formulations, wherein the formulations comprising or consisting said glucosamine, salt or a derivative thereof as the contrast agent.

In another aspect, the invention provides use of glucosamine and/or a salt and/or a derivative thereof in a method of imaging, said method comprising administering to a subject whose imaging is desired a formulation comprising glucosamine and/or a salt and/or a derivative thereof and imaging said subject.

In formulations of the invention, the glucosamine and/or a salt and/or a derivative thereof may be used as a single contrast agent or in combination with at least one additional contrast agent, provided that imaging is at least partially based on the distribution of glucosamine and/or a salt and/or a derivative thereof in the subject's body. Determining which glucosamine to utilize or which combination of glucosamine and/or a salt and/or a derivative thereof to utilize or whether a combination of two or more glucosamine derivatives should be used depends on a multitude of parameters that a medical practitioner may know to consider. Such parameters may be based, inter alia, on subject-related considerations and/or therapy-related considerations, such as the subject to be treated (age, sex, etc), the subject's general health, the disease type to be imaged, the region of the subject's body to be imaged, the characterization of the imaging period, the duration of imaging, the dosage required to achieve an effective imaging and diagnosis, and others.

In some embodiments, the diagnostic formulation comprises or consists, as the contrast agent, glucosamine and/or a salt and/or a derivative thereof.

The glucosamine derivative is selected from N-alkyl glucosamine, N,N'-dialkyl glucosamine, higher N-substituted or N,N'-disubstituted derivatives and salts of glucosamine, wherein the alkylating group in the N-alkyl or N,N'-dialkyl derivatives is selected amongst $C_1$-$C_5$alkyl derivatives (methyl ethyl, propyl, butyl, pentyl, isobutyl, isopropyl, and others). Non-limiting examples include N-methyl glucosamine, N,N'-dimethyl glucosamine and N-acylglucosamine. In some embodiments, the glucosamine derivative is not N-acetylglucosamine.

The glucosamine salt may be a pharmaceutically acceptable and diagnostically effective acid addition salt derived from inorganic acids such as hydrochloric, nitric, phosphoric, sulfuric, hydrobromic, hydriodic, phosphorous and others, as well as salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids and others. Such salts include sulfate, pyrosulfate, bisulfate, sulfite, bisulfite, nitrate, phosphate, mono-hydrogenphosphate, di-hydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate and others.

The glucosamine salts may be prepared by contacting the free base glucosamine with a sufficient amount of the desired acid to produce the salt in the conventional manner.

In some embodiments, the glucosamine salt is selected from glucosamine sulfate and glucosamine hydrochloride.

In some embodiments, the formulation comprises a combination of glucosamine and at least one additional contrast agent, said additional contrast agent being selected from glucosamine derivatives or salt, as defined, and contrast agents known in the imaging of specific disease states.

As detailed herein, the diagnostic formulation of the invention may be used in imaging for detecting, diagnosing or monitoring a disease state in a subject's body or in an organ or tissue obtained or derived from a subject (human or non-human). In some embodiments, the formulation is for imaging at least one body region of a subject. The body region may be the whole body, any part of the body, any one or more regions of the body or any tissue or organ. Therefore, formulations of the invention may be adapted or configured for any administration route, including, inter alia, oral (PO), topical, transdermal, parenteral (IP) and intravenous (IV) administration. In some embodiments, the formulation is adapted or configured for oral administration, e.g., as a diagnostically pre-formulated composition or as a ready for use formulation.

The administration may be performed inside or outside the imaging unit, e.g., MRI scanner, immediately prior to, or during the course of imaging.

In some embodiments, the formulation is adapted or configured for administration by infusion or generally by injection.

The injectable formulation comprising glucosamine or a derivative thereof, as defined herein, is optionally for use in imaging.

The injectable formulation comprising glucosamine and/or a salt and/or a derivative thereof may be utilized in method of therapeutic treatment or diagnosis, as may be necessitated. The injectable formulation is suitable for injection into a human or animal subject by any known means. It may be prepared pre-mixed, ready-to-use, as a dilute formulation or in a concentration for immediate use, without dilution, or as a concentrate for dilution with a suitable diluent or carrier. The formulation may be administered by parenteral routes, including, subcutaneous, intramuscular, and intravenous routes.

In some embodiments, the formulation is adapted for intravenous administration to a subject, e.g., direct bolus intravenous administration.

In some embodiments, the formulation is administered intravascularly using an injector or an infusion pump or any other device for intravascular administration known to those skilled in the field.

Generally speaking, the glucosamine, salt and/or derivative thereof may be administered orally in solution or as a solid pure glucosamine, salt and/or derivative. When made into formulations, the formulations of the invention may comprise a diagnostically acceptable carrier, diluent or excipient, suitable for use in diagnosis, particularly in imaging. The carrier may be water-based, e.g., an aqueous solution, or an oil-based carrier solution containing the contrast agent and an organic or oil-based carrier or agent. The choice of carrier will be determined in part by the particular method used to administer the formulation. Accordingly, there is a wide variety of suitable formulations of the present invention. The following formulations for oral and intravenous administration are merely exemplary and are in no way limiting.

Formulations suitable for oral administration may consist of (a) liquid solutions, such as an effective amount of the contrast agent dissolved in diluents, such as water, saline, or orange juice; (b) capsules, sachets, tablets, lozenges, and troches, each containing a predetermined amount of the contrast agent, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the contrast agent in a flavor, usually sucrose and acacia, as well as pastilles comprising the active ingredient in an inert base, such as gelatin and glycerin, or sucrose and acacia, emulsions, gels, and the like containing, in addition to the contrast agent, such carriers as are known in the art.

Formulations suitable for administration by injection may include aqueous and non-aqueous, isotonic sterile injection solutions, which can contain anti-oxidants, buffers, bacteriostats, and solutes that render the formulation isotonic with the blood of the subject recipient, and aqueous and non-aqueous sterile suspensions that include suspending agents, solubilizers, thickening agents, stabilizers, and preservatives. The contrast agent can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils for injectable formulations include petroleum, animal, vegetable, or synthetic oils. Specific examples of oils include peanut, soybean, sesame, cottonseed, corn, olive, petrolatum, and mineral. Suitable fatty acids for use in such formulations include oleic acid, stearic acid, and isostearic acid. Ethyl oleate and isopropyl myristate are examples of such fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

The parenteral formulations will typically contain from about 0.5 to about 25% by weight of the contrast agent in solution. Suitable preservatives and buffers can be used in such formulations. In order to minimize or eliminate irritation at the site of injection, such formulations may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Formulations of the invention may be formulated as solid formulations suited for reconstitution in a liquid diluent or carrier.

The disease or disorder to be diagnosed, monitored or detected, by any one imaging method of the invention, may be any disease or disorder that involves a high rate of glycolysis in a tissue region or a low rate of glycolysis in a tissue region as compared to other neighboring or vicinal tissue regions. In some embodiments, the disease or disorder is selected from proliferative diseases or disorders, characterized by abnormal cell proliferation.

As glucosamine has been shown to penetrate the brain-blood-barrier, imaging of brain pathologies has become possible [6]. In some embodiments, the disease or disorder is selected from neurodegenerative disorders. In some embodiments, the method of imaging may further comprise imaging of the brain.

In some embodiments, the proliferative disease or disorder is cancer. As used herein the term "cancer" relates to a neoplastic disease which is characterized by abnormal and uncontrolled cell division causing malignant growth or tumor. Cancer includes the two broad categories of carcinoma and sarcoma.

In some embodiments, the cancer is selected amongst cancerous states of skin tissues, organs, blood and blood vessels, which include cancers of the bladder, bone, blood, brain, breast, cervix, chest, colon, endrometrium, esophagus, eye, head, kidney, liver, lymph node, lung, mouth, neck, ovary, pancreas, prostate, rectum, stomach, testicles, throat or uterus.

In some embodiments, the cancer is a solid tumor or tumor metastasis.

In some embodiments, the cancer is selected from lung cancer, pancreatic cancers, colon cancers, prostate cancer including the advanced disease, hematopoietic tumors of lymphoid lineage, thyroid follicular cancer, myelodysplastic syndrome (MDS), tumors of mesenchymal origin, melanomas, teratocarcinomas, neuroblastomas, gliomas, glioblastoma, benign tumor of the skin, breast carcinoma, kidney carcinoma, ovary carcinoma, bladder carcinoma and epidermal carcinoma.

In some embodiments, the cancer includes advanced malignancy, amyloidosis, neuroblastoma, meningioma, hemangiopericytoma, multiple brain metastasis, glioblastoma multiformis, glioblastoma, brain stem glioma, poor prognosis malignant brain tumor, malignant glioma, recurrent malignant glioma, anaplastic astrocytoma, anaplastic oligodendroglioma, neuroendocrine tumor, adenocarcinoma, Dukes C & D colorectal cancer, unresectable colorectal cancer, metastatic hepatocellular carcinoma, Kaposi's sarcoma, karotype acute myeloblastic leukemia, Hodgkin's lymphoma, Non-Hodgkin's lymphoma, cutaneous T-cell lymphoma, cutaneous B-cell lymphoma, diffuse large B-Cell lymphoma, low grade follicular lymphoma, malignant melanoma, malignant mesothelioma, malignant pleural effusion mesothelioma syndrome, intraperitoneal carcinoma, papillary serous carcinoma, gynecologic sarcoma, soft tissue sarcoma, scelroderma, subcutaneous vasculitis, Langerhans' cell histiocytosis, leiomyosarcoma, fibrodysplasia ossificans progressive, hormone refractory prostate cancer, resected high-risk soft tissue sarcoma, unrescectable hepatocellular carcinoma, Waldenstroms macroglobulinemia, smoldering myeloma, indolent myeloma, salpinx cancer, androgen-dependent prostate cancer, androgen-dependent stage IV non-metastatic prostate cancer, hormone-insensitive prostate cancer, chemotherapeutic-insensitive prostate cancer, papillary thyroid carcinoma, follicular thyroid carcinoma, medullary thyroid carcinoma, and leiomyoma, and head and neck cancer.

In some embodiments, the disorder is a wound or atherosclerotic plaques.

In some embodiments, the disorder is a brain tumor or a brain pathology.

In some embodiments, the disease or disorder is a neurodegenerative disorder selected from diseases or conditions characterized by diminished movement capabilities and/or conditions which affect cognitive abilities. In some embodiments, the neurodegenerative disorder is selected from Alzheimer's disease, dementia, attention deficit, agitation, mild cognitive impairment, cognitive decline, memory loss, senility, olfactory impairment, diffuse Lewy body type Alzheimer's disease, Parkinson's disease, frontotemporal dementia, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, amyotrophic lateral sclerosis, Huntington's disease, brain injuries, as well as ischemia and stroke.

In some embodiments, the neurodegenerative disorder is selected from Alzheimer's disease and mild cognitive impairment. Glucose metabolism is known to be impaired in these syndromes, a fact which serves as the basis of their diagnosis by PET.

The ability of, e.g., glucosamine, to pass the blood-brain barrier and enter the brain established basis for assuming that their metabolism will be different in the case of these syndromes, thus rendering their imaging.

As the glucosamine, a derivative thereof or a combination of the two do not affect blood glucose levels or insulin sensitivity and are generally non-toxic, they may be used in diagnosis of subjects who suffer from background or secondary diseases or disorders, including diabetes.

In some embodiments, the formulation is for determining the site of a disease and/or for distinguishing between healthy and abnormal tissues or organs.

In some embodiments, the formulation is for distinguishing or differentiating between malignant and benign tumors.

In some embodiments, the formulation is for monitoring a disease state in a subject. In some embodiments, monitoring of a disease stage is directly or indirectly achievable by monitoring the level of metabolism of any one organ directly or indirectly associated with the disease.

The amount of a contrast agent according to the invention that may be used in any diagnostic method, or generally in any method of use, may be determined by the practitioner to provide an effective diagnosis, e.g., imaging. As contrast agents of the invention are non-toxic, the amount or dosage selected may be such to yield an effective end result. In some embodiments, the dosage, e.g., for oral administration may be between 0.2 and 10 grams per body weight or per day. In other embodiments, the dosage may be from about 0.2 grams to about 5 grams per body weight, from about 0.5 grams to about 3 grams or from about 0.5 grams to about 5 grams per body weight.

In other embodiments, the dosage is from about 0.5 grams to about 20 grams per body weight, from about 0.8 grams to about 15 grams, from about 1 gram to about 10 grams, from about 1 gram to about 8 grams, from about 1 gram to about 5 grams or from about 1.5 gram to about 3 grams per body weight.

In some embodiments, the dosage is at least 0.5 gram/body weight, least 1 gram/body weight or at most 20 gram/body weight.

In some embodiment, the dosage is about 2 gram per body weight.

As used herein, "body weight" generally refers to an average weight of a human subject, being about 70 Kg. The weight may be different and thus the dosage size may vary accordingly.

Similarly, when administered by other administration routes, such as IV, the dosage may vary accordingly. In some embodiments, the IV or infusion dosage is at least 0.5 gram/body weight, least 1 gram/body weight or at most 20 gram/body weight.

In some embodiments, the IV or infusion dosage is between 0.2 and 10 grams per body weight or per day. In other embodiments, the dosage may be from about 0.2 grams to about 5 grams per body weight, from about 0.5 grams to about 3 grams or from about 0.5 grams to about 5 grams per body weight.

In other embodiments, the IV or infusion dosage is from about 0.5 grams to about 20 grams per body weight, from about 0.8 grams to about 15 grams, from about 1 gram to about 10 grams, from about 1 gram to about 8 grams, from about 1 gram to about 5 grams or from about 1.5 gram to about 3 grams per body weight.

In some embodiments, the IV or infusion dosage is at least 0.5 gram/body weight, least 1 gram/body weight or at most 20 gram/body weight.

In some embodiment, the IV or infusion dosage is about 2 grams per body weight.

In some embodiments, the IV or infusion dosage is below about 1 gram per body weight or imaging protocol. In some embodiments, the IV or infusion dosage is between 0.5 grams and 10 grams per body weight or imaging protocol.

In another aspect, the invention provides a method for imaging at least one body region of a subject, the method comprising administering to said subject an effective amount of a contrast agent selected from glucosamine, salt thereof and a derivative thereof, and imaging said at least one body region, wherein glucosamine, salt thereof or a derivative thereof is the only (or main) contrast agent.

In some embodiments, the method of the invention is utilized for determining a site of a disease and/or for distinguishing between healthy and abnormal tissues or organs. In some embodiments, the method is used for distinguishing or differentiating between malignant and benign tumors.

In a further aspect, the invention provides a method for diagnosis of a disease or disorder in a subject, said method comprising administering to the subject a diagnostically effective amount of a contrast agent selected from glucosamine, salt thereof and a derivative thereof, and imaging the subject or a body region of the subject to thereby identify body regions in which said glucosamine, salt thereof or a derivative thereof has been localized, wherein optionally the glucosamine, salt thereof or a derivative thereof is the only contrast agent.

As glucosamine, a salt or a derivative thereof may be utilized for imaging a region or organ of a subject's body after or during treatment or otherwise state of a disease, it may be further utilized in determining severity of the disease, for, e.g., enabling determination of treatment effectiveness and continued treatment. Therefore, the contrast agents of the invention may be further utilized in a method for monitoring a disease state in a subject. In such a method, the subject is administered with glucosamine, salt thereof and/or a derivative thereof, the subject's body or any one or more regions thereof is imaged, to obtain at least one imaging parameter indicative of the disease or disorder state, and comparing said at least one imaging parameter to at least one parameter obtained from said subject at an earlier point in time or upon identification of, e.g., at least one symptom associated with said disease or disorder, wherein the comparison permits determining the progression of the disease or disorder state.

Effective monitoring, made possible by utilization of contrast agents of the invention, involves obtaining multiple parameters indicative of a disease state and progression at various points in time, prior to, during or after commencement of treatment, and comparing the collected data to determine any one therapeutic parameter. The monitoring may be conducted over a period of time, for example every few days or weeks, once a week, once a month, at the onset of treatment and at any time thereafter, etc.

Imaging and collection of imaging parameters for enabling any of the imaging methods of the invention, may be achieved by any one or more imaging methods known to a nuclear medicine technician. Such methods may be selected from magnetic resonance imaging (MRI), positron emission tomography (PET), radiology (X-ray), ultrasound, computed tomography (CT) and fluorescent imaging.

In some embodiments, the imaging method is positron emission tomography (PET).

In some embodiments, the imaging method is MRI. In some embodiments, MRI is selected from chemical exchange saturation transfer (CEST) MRI, chemical exchange spin lock (CESL) MRI, diffusion MRI, magnetic resonance angiography, dynamic contrast-enhanced MRI (DCE) MRI and positron emission tomography (PET).

In some embodiments, the MRI is chemical exchange saturation transfer (CEST) MRI.

In addition to the above imaging methods, monitoring may be achieved by any other imaging technique or any one diagnostic method. In some embodiments, the monitoring is conducted by pulse sequence of gradient echo. In other embodiments, the monitoring is conducted by MRI pulse sequences, enabling, e.g., measurement of changes in tumor's metabolism as a result of exposure to a contrast agent according to the invention. In further embodiments, monitoring is conducted by EPI (echo planar imaging), spin echo (RARE) or any other pulse sequence that yields high resolution image contrast.

Imaging parameters collected for enabling any method of the invention may include any measurable parameter obtainable using any imaging technique available. Examples of such parameters include, inter alia, images (e.g. four-dimensional images or pictures of functional processes in the body) acquired by a nuclear medicine technician, magnetic resonance imaging (MRI), positron emission tomography (PET), radiology (X-ray), ultrasound, computed tomography (CT) or fluorescent imaging.

In a further aspect, the invention provides a method for determining the severity of a disease or disorder in a subject, the method comprising administering to said subject glucosamine, salt thereof and/or a derivative thereof, imaging the subject's body or region thereof to obtain at least one imaging parameter (e.g., indicative of the state of the disease or disorder), and comparing said at least one imaging parameter to at least one parameter obtained from said subject at the onset of treatment or prior to treatment commencement, wherein the comparison permits determining the severity of the disease or disorder in the subject.

In another aspect the invention provides a method for determining the effectiveness of a therapeutic treatment of a disease or disorder in a subject, the method comprising administering to said subject glucosamine, salt thereof and/or a derivative thereof, imaging the subject's body or region thereof to obtain at least one imaging parameter (e.g., indicative of the state of the disease or disorder), and comparing said at least one imaging parameter to at least one parameter obtained from said subject at the onset of treatment or prior to treatment commencement, wherein the comparison permits determining the effectiveness of the therapeutic treatment of the disease or disorder in the subject.

The determination of the effectiveness of treatment may be achieved at the end of treatment or at any point in time during the treatment period. Generally, and depending on the disease and disease state, the effectiveness is indicated by any one or more changes in the disease state or any symptom associated therewith, such as decreased proliferation.

In some embodiments, the methods of the invention are used for evaluating the effectiveness of drug treatment in cancer treatment, for example, in evaluating the ability of a drug to reduce the size of a tumor or to prevent the tumor from growing, wherein the method comprises imaging the tumor with an imaging agent, as disclosed herein, and measuring the size of the tumor; administering the drug to the subject to affect at least one of reduction in the size of the tumor and prevention of growth of the tumor; re-imaging the tumor with the same or different glucosamine derivative and measuring the size of the tumor, and comparing the size of tumor after administration of the drug to the size of the tumor prior to administration of the drug.

In another aspect, the invention provides a diagnostic kit, the kit comprising glucosamine, salt thereof and/or a derivative thereof, or a formulation comprising same; and instructions for diagnostic use.

The invention further provides a toolkit that includes a solution of glucosamine, salt thereof and/or a derivative thereof, or a glucosamine, salt thereof and/or a derivative thereof in a solid form or as a liquid food form, in a concentration effective for imaging, e.g., in an amount sufficient for MR detection. The toolkit may comprise the glucosamine, salt thereof and/or a derivative thereof in ampules or solid form for use either with an available MR-compatible injector or an infusion pump or as an oral contrast agent.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A and FIG. 1B: CEST plots as a function of the offset at pH=7.4 (pH dependencies of the CEST of GlcN sulfate solution at an offset of 1.2 ppm from the water signal). FIG. 1C and FIG. 1D The pH dependencies of the CEST of GlcN sulfate and GlcNAc solutions, respectively, at an offset of 1.2 ppm from the water signal.

FIG. 2A: A $T_2$-weighted image before the administration of the agent (the conventional image). FIG. 2B: A CEST image before the administration of the agent (10% CEST in the tumor). FIG. 2C: A CEST image 36 min after administration (18.8% CEST in the tumor, significant CEST contrast at areas suspected to be metastasis). The marked ROI was used for the CEST calculation. FIG. 2D: % CEST obtained by different glucosamine dose treatment.

FIG. 6A: A $T_2$ weighted image before the administration of the agent. FIG. 6B: A CEST image before the administration of the agent. FIG. 6C: A CEST image 11 min after treatment. FIG. 6D: A CEST image 46 min after treatment.

FIG. 7A: A $T_2$ weighted image before the administration of the agent. FIG. 7B: A CEST image before the administration of the agent. FIG. 7C: A CEST image 15 min after treatment. FIG. 7D: A CEST image 60 min after treatment.

FIGS. 8IA-C and 8IIA-C provide images of CEST MRI kinetic measurements in MCF7 tumors (human cancer cells) at different times following IV (FIG. 8I) and PO (FIG. 8II) administration of glucosamine, 1 g/kg. ($B_1$=2.5 µT, $B_0$=7 T). FIG. 8IA: A $T_2$ weighted image before the administration of the agent. FIG. 8IB: A CEST image before the administration of the agent. FIG. 8IC: A CEST image 73 min after treatment. FIG. 8IIA: A $T_2$ weighted image before the administration of the agent. FIG. 8IIB: A CEST image before the administration of the agent. FIG. 8IIC: A CEST image 72 min after treatment.

FIG. 9A: $T_2$ MRI image featuring a frontal slice through a mouse brain. FIG. 9B: CEST contrast before administration of glucosamine. FIG. 9C: CEST contrast obtained 7 min. after administration with glucosamine, 1.5 g/kg (IP). FIG. 9D: Representative CEST contrast obtained 47 min. after administration with glucosamine 1.5 g/kg (IP), *in the cortex.

DETAILED DESCRIPTION OF EMBODIMENTS

Glucose and its analogues are known to be taken up preferentially by cancer cells.

The present invention provides means and methods for imaging, diagnosing and detecting tumors and metastases in earlier stage in human or animal subjects. The invention relates to techniques for imaging the Chemical Exchange Saturation Transfer (CEST) effect caused by the exchange of hydroxyl protons of the administrated glucosamine (or its derivatives) with bulk water in the body, enabling the generation of an amplified MR signals of tumors and metastasis.

The imaging of tumors using CEST-MRI of glucosamine (or its derivatives thereof) is of great potential and is predicted to replace PET-CT in becoming a standard imaging modality for the detection of tumors and their metastases and their response to therapy.

EXAMPLES

Glucosamine CEST MRI and CNS

CEST MRI using glucosamine or its derivatives can be used as imaging biomarkers to differentiate and discriminate primary (as well as advanced) central nervous system changes. As glucosamine passes through the blood-brain barrier (BBB) it can be used to assess cellular function and metabolic activity, for the diagnosis and evaluation of cancer and neurodegenerative diseases, such as Alzheimer disease (AD). By exchanging proton magnetization between its hydroxyl groups (or amino group) and water, low-concentration metabolites can be detected via abundant water protons using $^1$H magnetic resonance imaging (MRI). Glucosamine CEST MRI method shows a distinct white matter, gray matter distribution and can demonstrate the feasibility of mapping relative changes in glucosamine concentration in vivo. For example, it is expected that compared to healthy brains (of controls subjects), in models of AD, a notable decrease in glucosamine CEST contrast in the areas of WM in the brain will be observed. Moreover, the glucosamine CEST technique maps the distribution of glucosamine in the brain at high resolution: as the Hippocampus is the primary region affected in the early AD pathology, more profound decrease in glucosamine CEST contrast is observed in the hippocampus compared to other regions. This method potentially provides a novel noninvasive biomarker for diagnosing the disease in preclinical stages.

For that purpose, animals having neurodegenerative disease, (for an example AD model) will be examined. Following glucosamine CEST MR imaging, Z spectra over an offset range from ±5 ppm will be acquired and MRTasym plots will be obtained and the results will be compared with healthy animals. It is expected that glucosamine CEST contrast will be significantly different in models of neurodegenerative diseases than in the control (healthy animals). For this reason, glucosamine CEST MR imaging has the ability to provide new insights into the role of glucosamine in the CNS as well as serve as a biomarker for diagnosis and treatment of CNS disorders.

In Vitro Studies of Glucosamine

NMR Spectroscopy:

NMR spectra were acquired on a Bruker DRX spectrometer (Germany), equipped with a 11.7 T wide-bore vertical magnet, operating at an RF of 500 MHz for $^1$H detection, using an inverse (TXI) probe handling 5 mm tube. The probe temperature was set to 37° C. for all experiments. The 45° pulse duration was ~16 µs (the spectrometer was de-tuned to avoid radiation damping effects); and the acquisition time (aq) and relaxation delay (di) were 8 s and 2 s, respectively. Spectral width of 7500 Hz, data size 16 K; number of scans=8. For the CEST experiments, a series of frequencies (Ω) were used in the range of −3.5 to +3.5 ppm relative to the water signal which was calibrated at 0 ppm. The pre-saturation pulse had duration of 3 s and several rf saturation fields ($B_1$) in the range of 1-6 µT were used. The data were recorded and processed using TOPSPIN 2.1 software (Bruker).

The chemical exchange contrast was measured by magnetization transfer asymmetry, MTRasym: MTRasym (Ω)= $[M_{CEST}(-\Omega) - M_{CEST}(\Omega)]/M_0$.

Example 1: % CEST Obtained with Physiological Solution of Glucosamine

% CEST obtained with physiological solution of glucosamine.

Figure 1A:
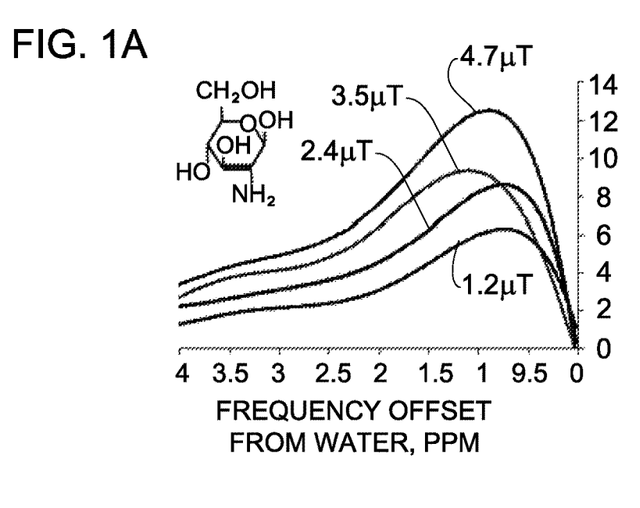
FIGS. 1A-D provide radiofrequency (RF) saturation field ($B_1$) and pH dependencies of CEST contrast in 20 mM GlcN sulfate and GlcNAc solutions (containing 10 mM PBS and 10% $D_2O$) at a temperature of 37° C. at 11.7 T.

The % CEST plot for 20 mM glucosamine at pH of 7.4 and temperature of 37° C. at different rf saturation fields ($B_1$) is shown in FIG. 1A. The lack of resolution in the plot is a result of the extensive broadening due to enhanced chemical exchange at this pH and temperature. A simple calculation indicates that because the proton concentration in water is 111 M, ~7% CEST for a glucosamine concentration of 20 mM (at frequency offset of 1.2 ppm, $B_1$=2.4 µT) corresponds to enhancement factor of approximately 350 relative to the direct detection of glucosamine.

Figure 1B:
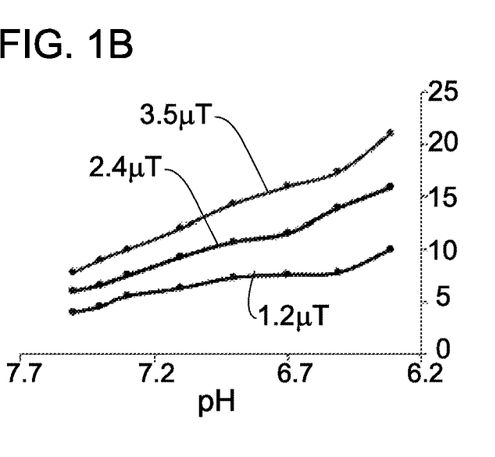
Figure 1C:
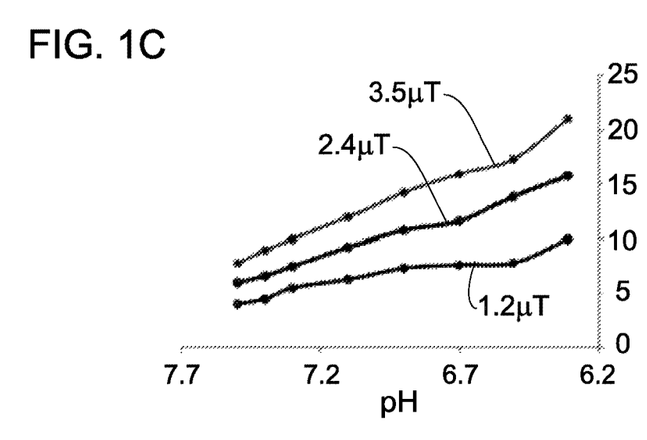
Figure 1D:
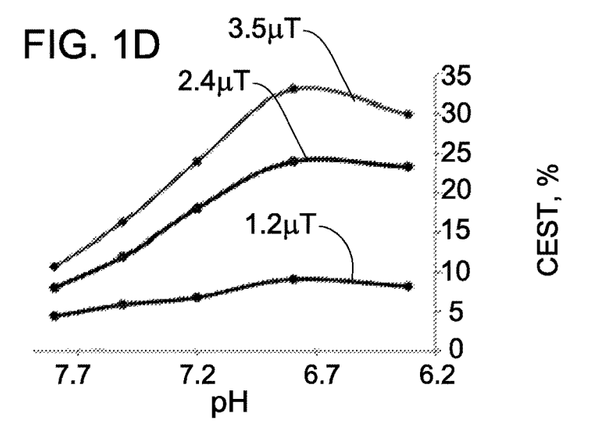
Figure 2A:
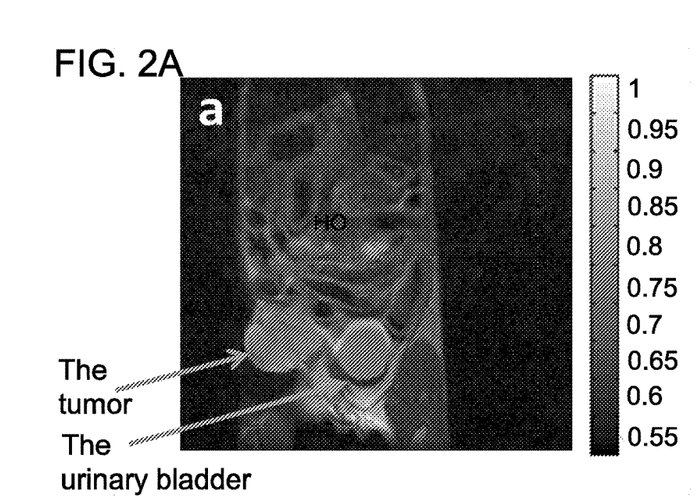
FIGS. 2A-D provide images of CEST MRI kinetic measurements in $4T_1$ tumor at different times following per os administration of glucosamine, 1.1 g/kg. ($B_1$=2.5 µT, $B_0$=7 T).
Figure 2B:
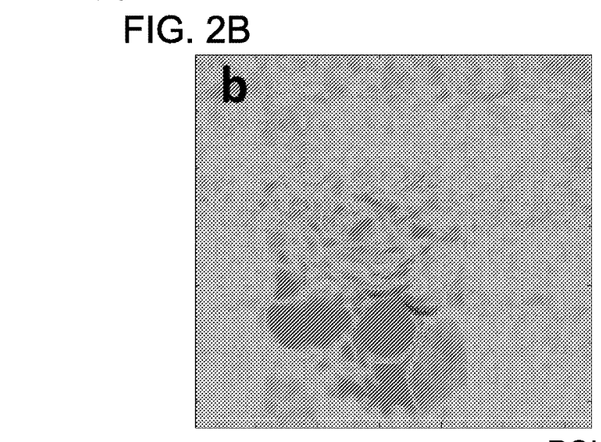
Figure 2C:
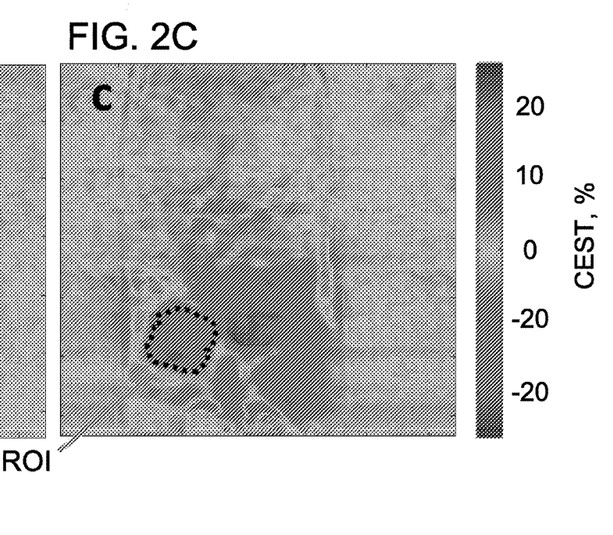
Figure 2D:
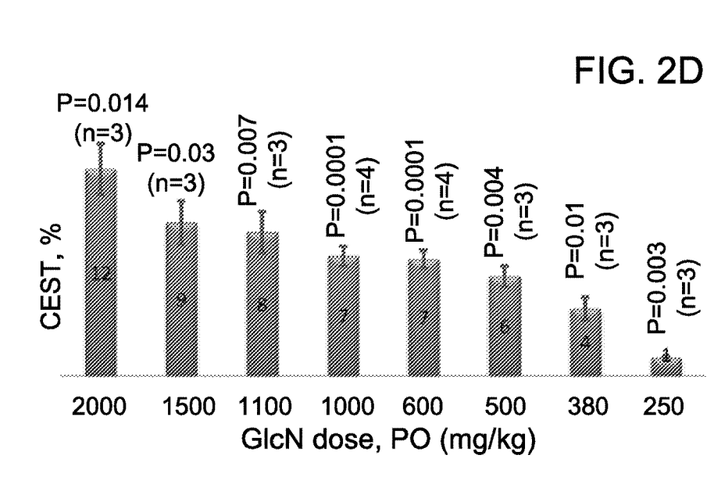

As can be seen from the pH dependence shown in FIG. 1B, the CEST effect is significantly larger at lower pH values, which may be pertinent to the extracellular microenvironment of tumors known to be slightly acidic. GlcN showed significant CEST effects through the amino protons at a frequency offset of ~3 ppm (FIG. 1A).

In Vivo Studies

Example 2: Imaging of Cancer Abnormalities

Figure 3:
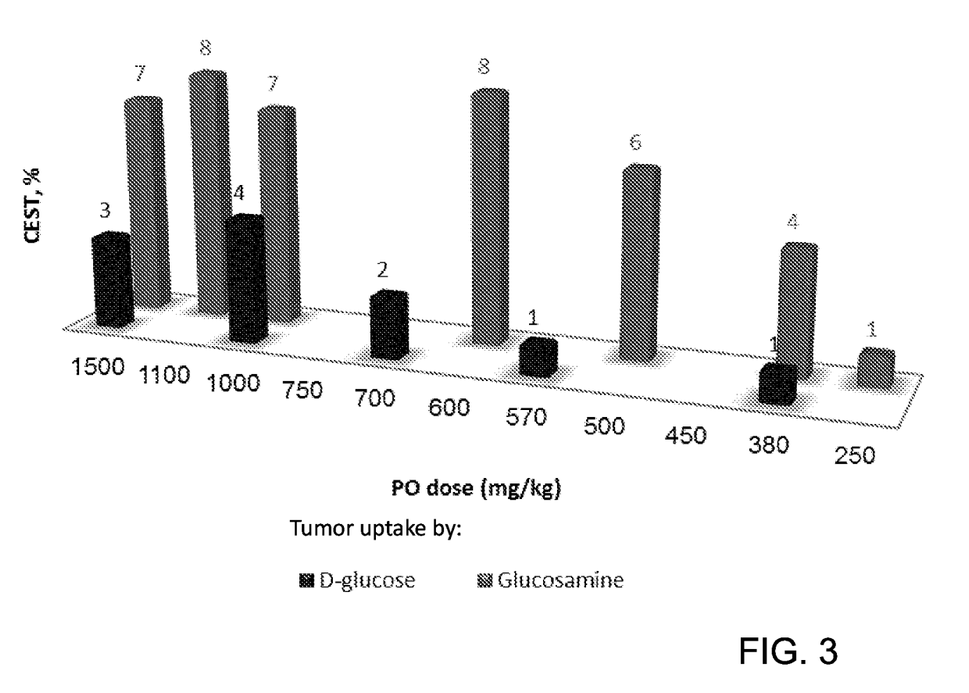
FIG. 3 is a graphical representation showing % CEST obtained with $4T_1$ model at different dose following PO administration of glucosamine vs. D-glucose.
Figure 4:
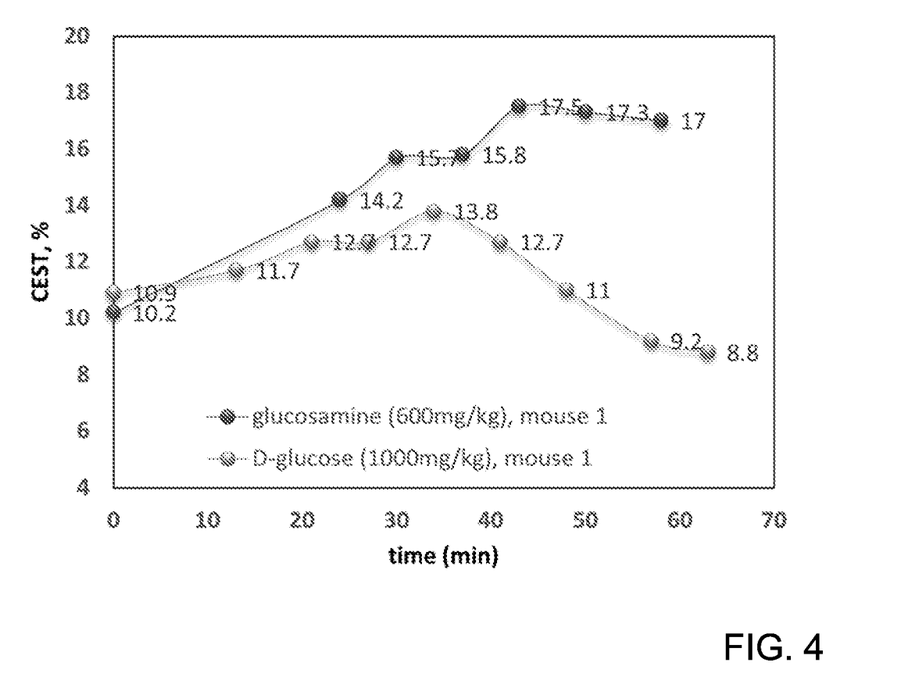
FIG. 4 is a graphical representation showing % CEST signal obtained with $4T_1$ tumor at different times following per os administration of glucosamine (600 mg/kg) and D-glucose (1,000 mg/kg) of the same animal.
Figure 5A:
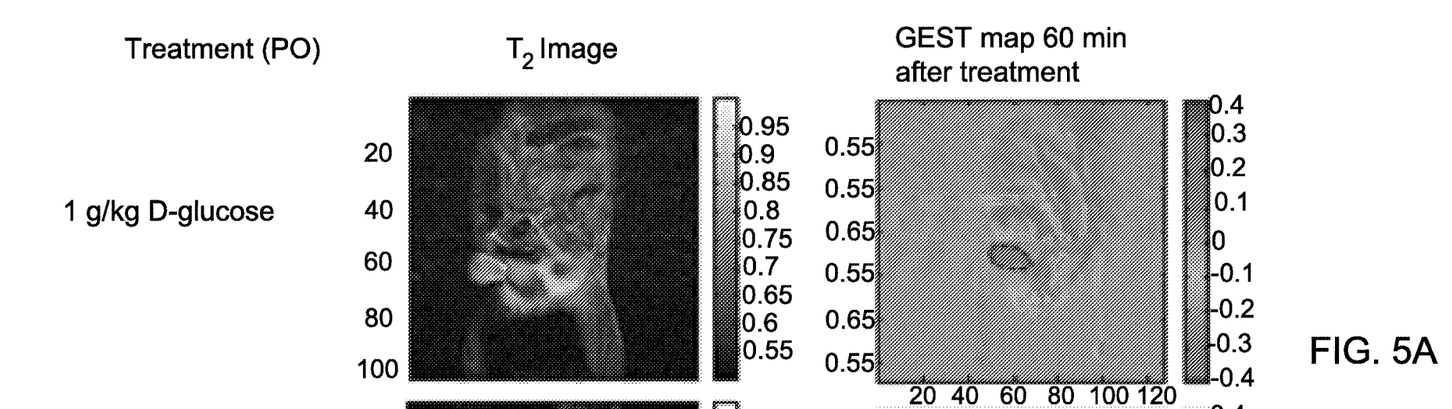
FIGS. 5A-B provide images of glucosamine uptake (FIG. 5B) vs D-glucose (FIG. 5A) by CEST MRI 60 minutes after administering.
Figure 5B:
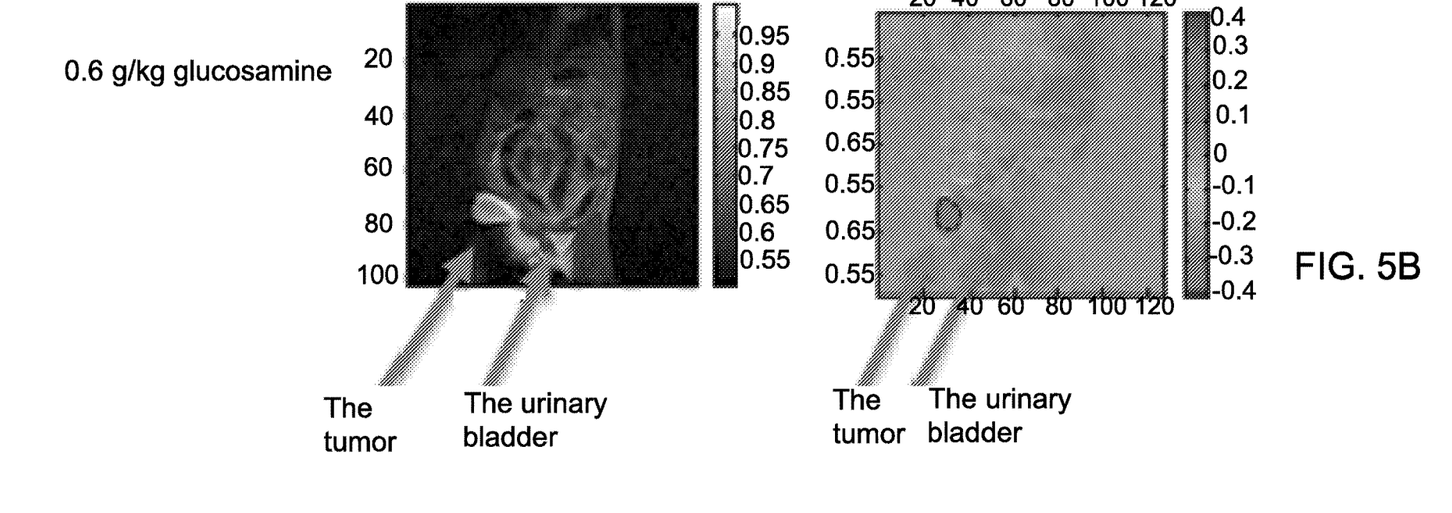
Figure 6A:
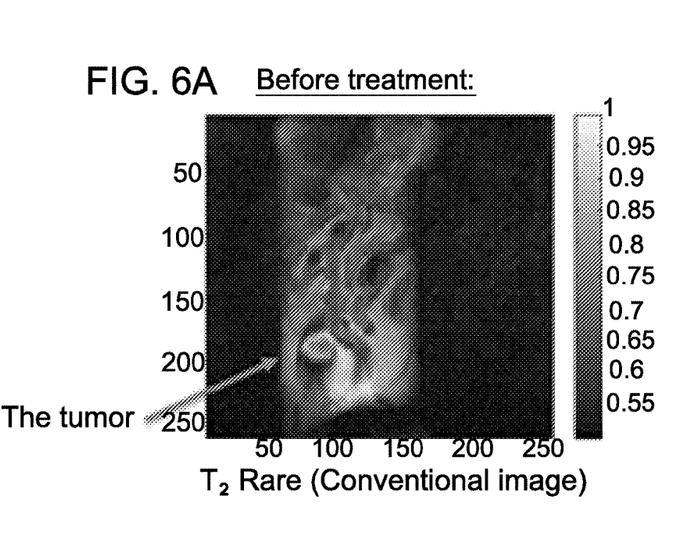
FIGS. 6A-D provide images of CEST MRI kinetic measurements in small primary $4T_1$ breast tumor at different times following PO administration of glucosamine, 0.38 g/kg. ($B_1$=2.5 µT, $B_0$=7 T).
Figure 6B:
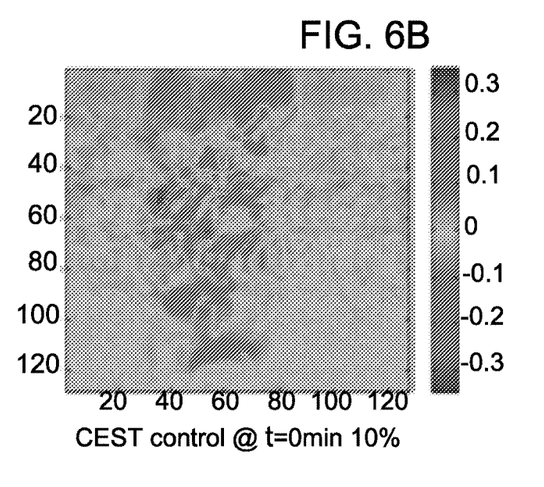
Figure 6C:
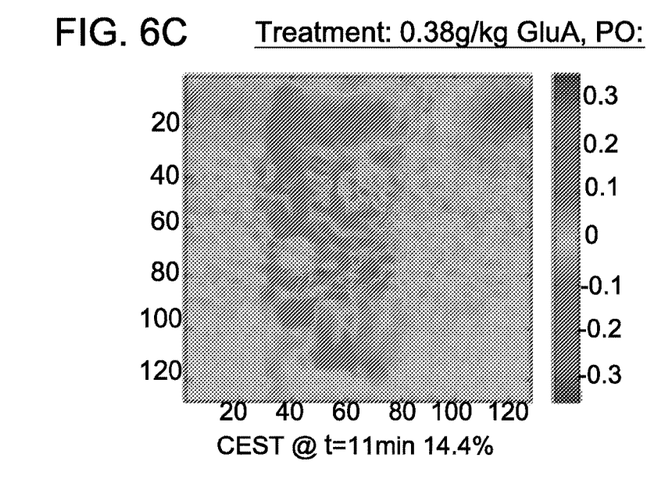
Figure 6D:
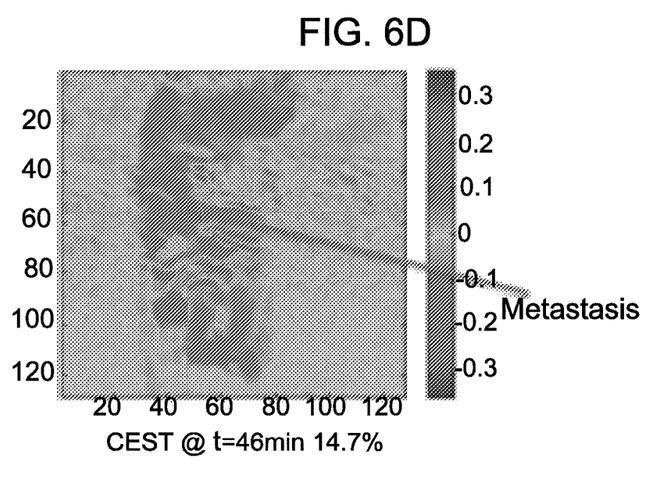
Figure 7A:
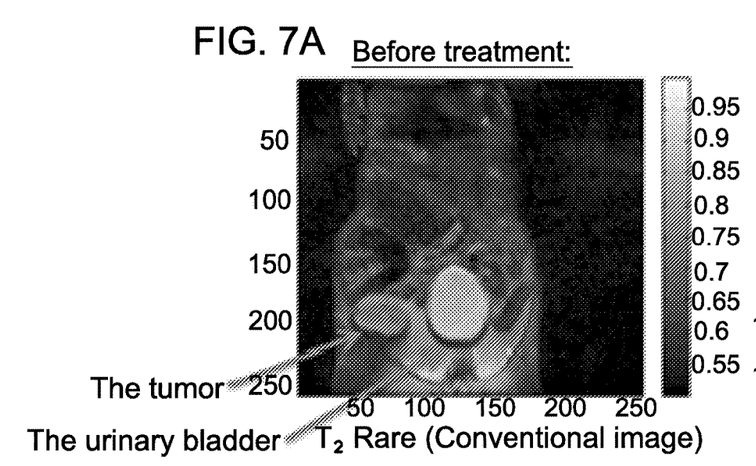
FIGS. 7A-D provides images of CEST MRI kinetic measurements in advanced stage of $4T_1$ breast tumor model before and after PO administering of 0.38 g per kg glucosamine ($B_1$=2.5 µT, $B_0$=7T).
Figure 7B:
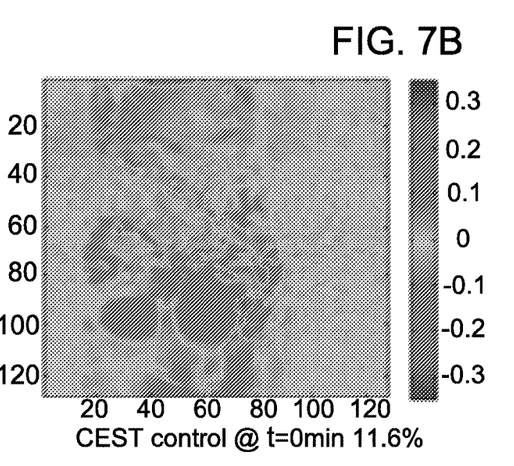
Figure 7C:
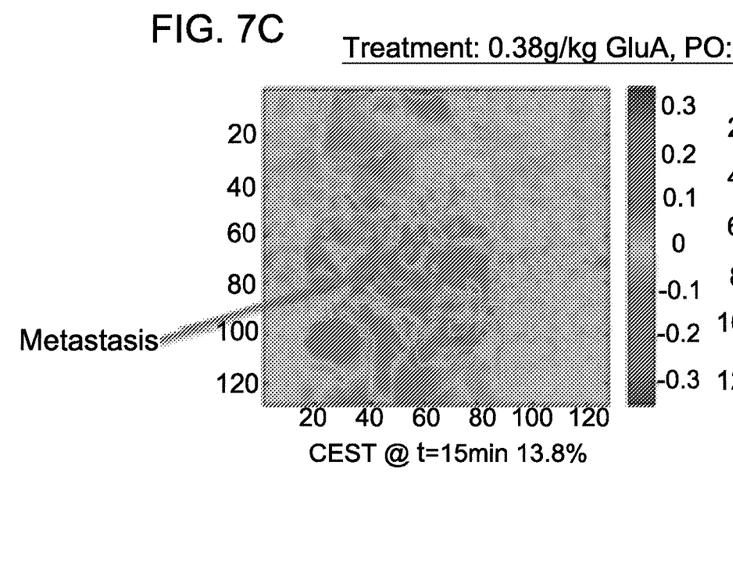
Figure 7D:
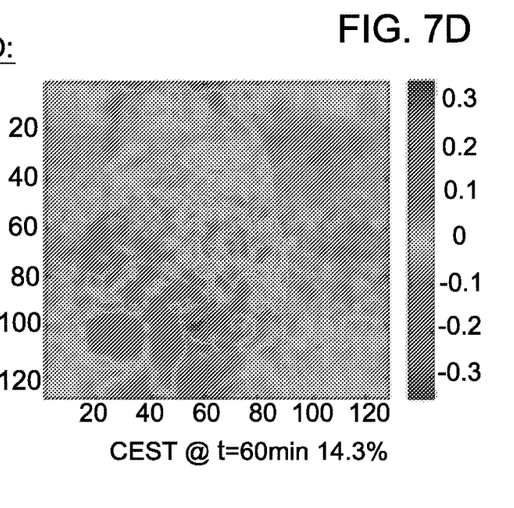
Figure 8:
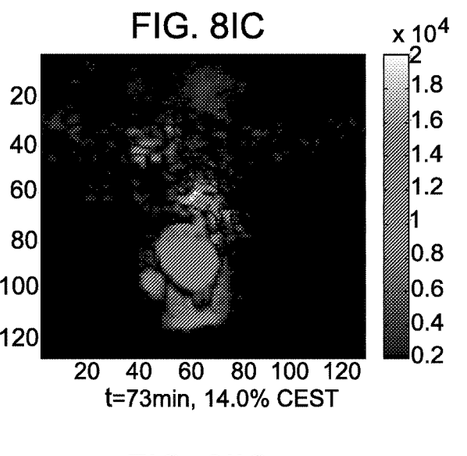
Figure 9A:
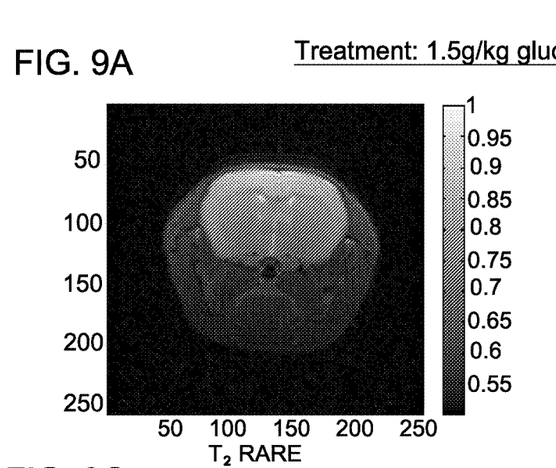
FIGS. 9A-D provide $T_2$ and CEST MRI images demonstrating uptake of glucosamine in healthy mouse brain.
Figure 9B:
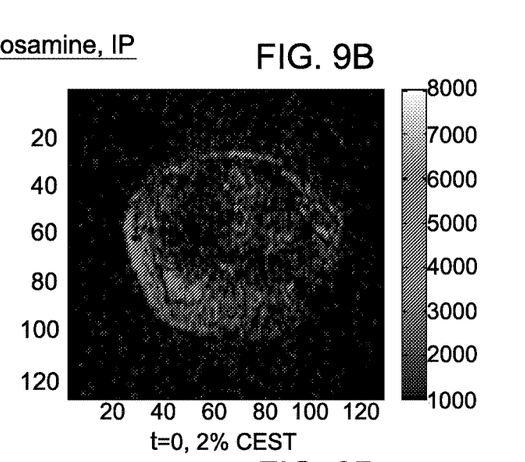
Figure 9C:
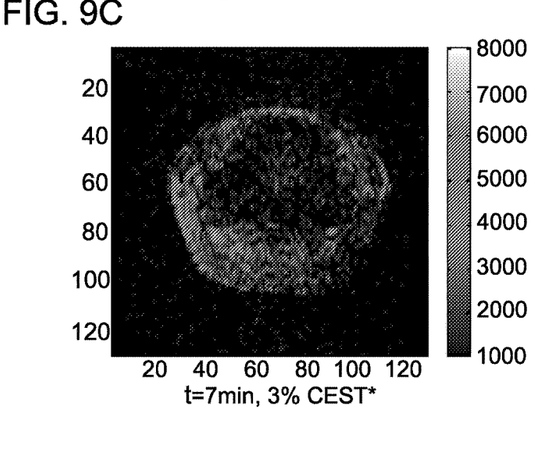
Figure 9D:
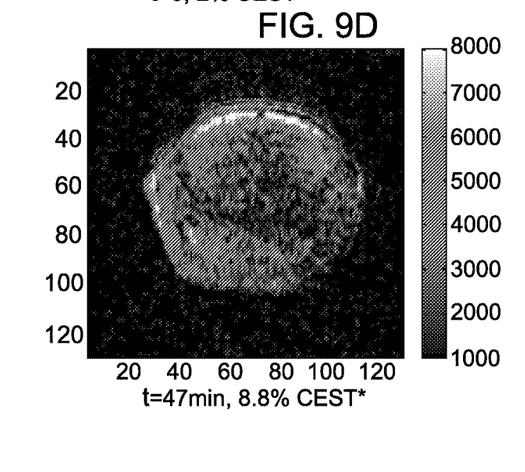

Chemicals and Media:
Glucosamine was obtained from Sigma-Aldrich, Israel.
Cells: 4T1 Breast Tumor Cells
$4T_1$ mouse mammary tumor cell lines were obtained from ATCC. Cells were cultured in high glucose DMEM supplemented 5% FBS, 5% NCS, NEAA and antibiotics (100 units/ml penicillin and 100 µg/ml streptomycin) at 37° C. in a humidified atmosphere containing 5% $CO_2$.
Animals:
Implantation of 4T1 Cancer Cells in Mice
BALB/C female mice were purchased and kept in the breeding facility of Life Science School, Tel Aviv University. To induce orthotropic xenograph tumors in the mice. $4T_1$ cells were injected into the lower left mammary gland of 8-week-old (17-22 gram) animals ($10^6$ cells in 100 µL saline). The tumors were allowed to grow for 10-14 days, reaching an average tumor volume of 5 $mm^3$. All experiments with animal models were carried out in compliance with the principles of the National Research Council (NRC) and were approved by the institutional animal care and use committee (IACUC) (#M-15-057).
The In Vivo CEST
A Bruker 7 Tesla (T) Biospec scanner with 30 cm bore size was used to scan implanted xenograph mammary tumors of mice before and after administration (i.v., i.p. or p.o.) of glucosamine or its derivatives (the glucose analogues were dissolved in saline, pH 7.4). $4T_1$ or MCF7 tumor-bearing mice, with an average tumor volume of 2-7 $mm^3$, were fasted overnight with water access, anesthetized with isoflurane (1-2%) and scanned (without surface coil). Their temperature was maintained at 37° C.
At first, $T_2$ RARE anatomical images (RARE factor-8, TR-3000 ms, TE-11.7 ms) were acquired to identify the slice selection with maximum tumor size. The CEST images were generated as follows: a series of $T_2$ RARE images (RARE factor-1, TR-3000 ms, TE-11.7 ms) were collected from a single 1 mm coronal slice of the abdominal area (acquisition matrix before zero filling 128×64, field of view of 40×40 $mm^2$) after a 2 s presaturation pulse of $B_1$=2.5 µT (106 Hz) at the hydroxyl proton frequency offset of ±1.2 ppm from the water signal. The CEST images were acquired before and after glucosamine or its derivatives administration in order to identify the baseline. The acquisition continued for more than an hour after treatment.
The mean intensities in the selected region of interest (ROI) of the tumor were used for the % CEST plot.
No corrections for the $B_0$ inhomogeneity were used in the present work because no significant change was observed after such correction in our previous works. The line width of the water peak was approximately 30-40 Hz.
The examples comprise administering glucosamine to mice carrying mammary tumors and observing very significant image enhancement of the tumors. Moreover the enhancement occurs only in the metabolic part of the tumors and was not observed in the necrotic regions.
FIG. 2 provides CEST MRI kinetic measurements in $4T_1$ tumor at different times following per os treatment of glucosamine, 1.1 g/kg. ($B_1$=2.5 µT, $B_0$=7 T). a: A $T_2$-weighted image before the administration of the agent (the conventional image). b: A CEST image before the administration of the agent (10% CEST in the tumor). c: A CEST image 36 min after treatment (18.8% CEST in the tumor).
As can be seen from FIG. 2, a short time after glucosamine administration (1.1 g/kg), a strong CEST effect was visualized at the tumor and at organs suspected to be metastasis. Other organs (apart from the urinary bladder) did not show any significant CEST effect throughout the MRI scans session.
After PO treatment with glucosamine to mice carrying implanted breast tumors, the tumors gave an enhanced CEST MRI image that started within a few minutes following treatments and persisted for over an hour, whereas the mice seemed to be unaffected by the treatment.
As can be seen from FIG. 3, glucosamine yielded a significant CEST signal at oral dose of 380 mg/kg while D-glucose yielded no significant CEST signal at doses of less than 1 g/kg. The CEST signal of glucosamine increased over the time due to accumulation of glucosamine phosphorylation products which also contributed to the CEST signal, thus the signal last for a few hours. D-glucose is rapidly metabolized and as a result escapes accumulation in the tumor, its CEST signal disappear within less than an hour.
The lowest detectable dose obtained with glucosamine utilizing CEST MRI imaging of $4T_1$ tumors was 380 mg/kg (FIG. 3) which is equivalent to 2 gr per 70 kg human subject.
As can be understood from FIG. 4, upon administration of glucosamine at a dosage of 600 mg/kg and D-glucose at a dosage of 1000 mg/kg (to the same animal), the glucosamine CEST signal increased over time due to accumulation of glucosamine phosphorylation products which also contributed to the CEST signal. Furthermore, the signal of glucosamine lasted over one hour, while the signal of D-glucose decreased dramatically 30-40 minutes following administration.
FIG. 5 provides imaging of glucosamine uptake vs. D-glucose by CEST MRI 60 minutes after administering.
As can be understood from FIG. 5, 60 minutes after administering of D-glucose, no CEST signal was observed, while imaging the same animal after administration with glucosamine, presented a significant CEST effect, with only half the dosage used with D-glucose.
FIG. 6 provides imaging of glucosamine at small primary $4T_1$ breast tumor model after PO administering 0.38 g per kg.
FIG. 7 provides imaging of glucosamine at advanced stage of $4T_1$ breast tumor model after PO administering 0.38 g per kg.
FIG. 8 provides CEST MRI kinetic measurements in MCF7 tumors (human cancer cells) at different times following IV (FIG. 8I) and PO (FIG. 8II) treatments with glucosamine, 1.0 g/kg. ($B_1$=2.5 µT, $B_0$=7 T). a: A $T_2$-weighted image before the administration of the agent (the conventional image). b: A CEST image before the administration of the agent. c: A CEST image 72-73 min after treatment.
As can be seen from FIG. 8, glucosamine yielded a significant CEST contrast in humane tumors by different methods of administration (4-6%, PO and IV).

Example 3: Imaging of Brain Pathologies

Chemicals and Media:
Glucosamine was obtained from Sigma-Aldrich, Israel.
Animals:
Healthy BALB/C female mice were purchased and kept in the breeding facility of Life Science School, Tel Aviv University. All experiments with animal models were carried out in compliance with the principles of the National Research Council (NRC) and were approved by the institutional animal care and use committee (IACUC) (#M-15-057).

The In Vivo CEST

A Bruker 7 Tesla (T) Biospec scanner with 30 cm bore size was used to scan brains of healthy mice before and after administration (IV or IP) of glucosamine or its derivatives (the glucose analogues were dissolved in saline, pH 7.4). The mice were fasted overnight with water access, anesthetized with isoflurane (1-2%) and scanned with body coil for transmission and a quadrature coil for reception. Their temperature was maintained at 37° C.

At first, $T_2$ RARE anatomical images (RARE factor-8, TR-3000 ms, TE-11.7 ms) were acquired to identify the slice selection. The CEST images were generated as follows: a series of $T_2$ RARE images (RARE factor-1, TR-3000 ms, TE-11.7 ms) were collected from a single 1 mm slice (acquisition matrix 128×128, field of view of 40×40 mm$^2$) after a 2 s presaturation pulse of $B_1$=2.5 µT (106 Hz) at the hydroxyl proton frequency offset of ±1.2 ppm from the water signal. The CEST images were acquired before and after glucosamine (or its derivatives) administration in order to identify the baseline. The acquisition continued for an hour after treatment.

The mean intensities in the selected region of interest (ROI) of the brain (mainly in the cortex) were used for the % CEST calculation.

No corrections for the $B_0$ inhomogeneity were used in the present work because no significant change was observed after such correction in our previous works. The line width of the water peak was approximately 30-40 Hz.

In vivo glucosamine CEST MRI experiments were performed on frontal brain of healthy mouse. The aim of this study was to investigate the uptake of glucosamine in the brain (glucosamine delivery across the BBB) and to test whether it could detect changes in the pattern of the metabolic profile after treatment. As can clearly can be seen from the analyzed data (FIG. 9), significant differences were observed in the metabolic pattern of healthy mice mainly in the cortex and striatum, before and after glucosamine treatment, evidencing a significant CEST effect.

FIG. 9 demonstrates that glucosamine uptake enables for diagnosis of glucose transport through the blood-brain barrier of mouse brain.

The invention claimed is:

1. A method for imaging at least one body region of a subject, the method comprising
   administering to said subject a formulation comprising an effective amount of glucosamine for imaging the at least one body region of the subject; and
   imaging said at least one body region, by a magnetic resonance imaging (MRI) method selected from chemical exchange saturation transfer (CEST) and chemical exchange spin lock (CESL), to identify body regions in which the glucosamine accumulates or body regions of altered metabolic activity.

2. The method according to claim 1, wherein the effective amount is a diagnostically effective amount for the imaging of said at least one body region to enable determining a site of a disease and/or for distinguishing between healthy and abnormal tissues or organs.

3. The method according to claim 1, wherein the effective amount is a diagnostically effective amount for the imaging of said at least one body region to enable diagnosis of a disease or disorder in a subject.

4. The method according to claim 1, wherein the effective amount is a diagnostically effective amount for the imaging of said at least one body region to enable evaluating state of a disease prior to, after or during treatment.

5. The method according to claim 1, wherein the effective amount is a diagnostically effective amount for the imaging of said at least one body region to enable determining severity of a disease or disorder.

6. The method according to claim 1, the glucosamine is administered orally or by injection.

7. The method according to claim 1, comprising
   said administering of the formulation comprising glucosamine, and
   said imaging of said at least one body region, wherein said imaging comprises imaging the subject's body or any one or more regions thereof to obtain at least one imaging parameter indicative of a disease or disorder state, and
   further comprising monitoring the disease or disorder state, said monitoring comprising comparing said at least one imaging parameter to at least one parameter indicative of the disease or disorder obtained from said subject at an earlier point in time which is prior to said administering and imaging.

8. The method according to claim 1 comprising
   said administering to said subject a formulation comprising glucosamine, and
   said imaging of said at least one body region, wherein said imaging comprises imaging the subject's body or region thereof to obtain at least one imaging parameter indicative of a state of a disease or disorder, and
   further comprising determining severity of the disease or disorder in the subject, said determining comprising comparing said at least one imaging parameter to at least one parameter indicative of the state of the disease or disorder obtained from said subject at an earlier point in time at the onset of a treatment of the disease or disorder or prior to commencement of the treatment of the disease or disorder,
   wherein the comparison permits determining the severity of the disease or disorder in the subject.

9. The method according to claim 1, comprising
   said administering to said subject a formulation comprising glucosamine, wherein said subject to which said formulation is being administered has received a therapeutic treatment of a disease or disorder, and
   said imaging of said at least one body region, wherein said imaging comprises imaging the subject's body or region thereof to obtain at least one imaging parameter indicative of a state of the disease or disorder, and
   further comprising determining the effectiveness of the therapeutic treatment of the disease or disorder in the subject, said determining comprising comparing said at least one imaging parameter to at least one parameter indicative of the state of the disease or disorder obtained from said subject at the onset of the treatment or prior to commencement of the treatment,
   wherein the comparison permits determining the effectiveness of the therapeutic treatment of the disease or disorder in the subject.

* * * * *